United States Patent [19]

Dargan et al.

[11] Patent Number: 5,994,116
[45] Date of Patent: Nov. 30, 1999

[54] HERPESVIRUS PRE-(VIRAL DNA REPLICATION) ENVELOPED PARTICLES

[75] Inventors: Derrick James Dargan, Glasgow; Arvind Hirabhai Patel, Motherwell; John Herbert Subak-Sharpe, Glasgow, all of United Kingdom

[73] Assignee: Medical Research Council, London, United Kingdom

[21] Appl. No.: 08/676,323

[22] PCT Filed: Jan. 25, 1995

[86] PCT No.: PCT/GB95/00156

§ 371 Date: Jul. 19, 1996

§ 102(e) Date: Jul. 19, 1996

[87] PCT Pub. No.: WO95/20049

PCT Pub. Date: Jul. 27, 1995

[30] Foreign Application Priority Data

Jan. 25, 1994 [GB] United Kingdom ............... 9401333

[51] Int. Cl.⁶ ................................................. C12N 7/04
[52] U.S. Cl. .................... 435/236; 435/237; 435/238; 435/239; 424/231.1
[58] Field of Search ................................ 435/236, 261; 424/229.1

[56] References Cited

U.S. PATENT DOCUMENTS 5,384,122  1/1995  Cunningham et al. ............. 424/231.1

FOREIGN PATENT DOCUMENTS

WO-A-92 13943  8/1992  WIPO .
WO-A-92 19748  11/1992  WIPO .

OTHER PUBLICATIONS

Dargan, D.J., et al., 1995, "Preps: Herpes Simplex Virus Type 1-Specific Particles Produced by Infected Cells When Viral DNA Replication is Blocked.", J. Virol. 69(8):4924–4932.

Roizman, B., 1996, "Herpesviridae", in *Field's Virology*, Third Edition, Fields et al., eds., Lippincott–Raven Publishers, Philadelphia, pp. 2221–2230.

Roizmen et al., B., 1996, "Herpes Simplex Viruses and their Replication", in *Field's Virology*, Third Edition, Fields et al., eds., Lippincott–Raven Publishers, Philadelphia, pp. 2231–2295.

Kutinova et al., 1988, "Placebo–controlled study with subunit herpes simplex virus vaccine in subjects suffering from frequent herpetic recurrences", Vaccine 6:223–228.

Sasadeusz et al. 1993, "Systemic Antivirals in Herpesvirus Infections", Dermatol. Therap. 11(1):171–185.

Mester et al., 1991, "The Mouse Model and Understanding Immunity to Herpes Simplex Virus", Rev. Infect. Dis. 13(Suppl. 11):S935–S945.

Godowski P. et al., Identification of a herpes simplex virus function tha represses late gene expression from parental viral genomes, J. Virol. 55(2):357–365, Aug. 1985.

Chin S. et al. Virucidal short wavelength ultraviolet light treatment of plasma factor VIII concentrate: Protection of proteins by antioxidents, Blood 86(11):4331–4336, Dec. 1995.

Roizman B, Sears A, Herpes simplex viruses and their replication in Fields Virology v2; Lippincott–Raven, 2231–2295, 1996.

Irmiere A, Gibson W, Isolation and characterization of a noninfectious virion–like particle released from cells infected with human strains cytomegalovirus; Virology 130, 118–133, 1983.

Szilagyi J, Cunningham C, Identification and characterization of a novel non–infectious herpes simplex virus–related particle; J. Gen. Virol. 72:661–668, 1991.

Rixon F, Addison C, McLauchlan J; Assembly of enveloped tegument structures (L particles) can occur independently of virion maturation in herpes simplex virus type 1–infected cells; J. Gen. Virol. 73: 277–284, 1992.

McLauchlan J, Rixon F; Characterization of enveloped tegument structures (L particles) produced by alphaherpesviruses; integrity of the tegument does not depend on the presence of capsid or envelope; J. Gen. Virol. 73, 269–276, 1992.

McLauchlin J, Addison C, Craigie M, Rixon F; Noninfectious L–particles supply functions which can facilitate infection by HSV–1; Virol. 190: 682–688, 1992.

McLean G, Rixon F, Langeland N, Haarr L, Marsden H; Identification and characterization of the virion protein products of herpes simplex virus type 1gene UL47, J. Gen. Virol. 71, 2953–2960, 1990.

(List continued on next page.)

*Primary Examiner*—Laurie Scheiner
*Assistant Examiner*—Jeffrey S. Parkin
*Attorney, Agent, or Firm*—Nixon & Vanderhye

[57] ABSTRACT

This invention is directed toward a new type of herpesvirus particle (e.g., HSV-1), herein designated pre-viral DNA replication enveloped particles (PREPS), and methods of preparing said particles. These particles are non-infectious and can be prepared reliably to a high ratio of HSV-1 PREPS to infectious virus of at least $10^7:1$. PREPS can be produced under conditions wherein viral DNA replication is blocked through the use of suitable drugs (e.g., acyclovir [ACV]; cytosine-β-D-arabinofuranoside [ara C]) or by using an HSV mutant defective in viral DNA synthesis. Compositions comprising HSV-1 PREPS are disclosed wherein said particles have the following characteristics: a) the PREPS lack a viral capsid; b) the PREPS lack viral DNA; c) the PREPS contain reduced quantities of the proteins 273K (VP1–2), 82/81K (VP13/14), 57K (VP17, gD), and 40K, as compared to HSV-1 L particles; and d) the PREPS contain increased quantities of the proteins 175K (VP4, IE3), 92/91K (VP11/12), and 38K (VP22), as compared to HSV-1 L particles. These particles are useful, inter alia, for the generation of HSV-specific immunological and diagnostic reagents.

4 Claims, 5 Drawing Sheets

OTHER PUBLICATIONS

Johnson P, MacLean C, Marsden H, Dalziel R, Everett R; The product of gene US11 of herpes simplex virus type 1 is expressed as a true late gene; J. Gen. Virol. 67:871–883, 1986.

Latchman D; Herpes simplex virus life cycle and the design of viral vectors; in Methods in Molecular Biology v8, Practical Molecular Virology, ed. Collins M; Humana Press, 1991.

Rixon F, McLaughlan J; Insertion of DNA sequences at a unique restriction enzyme site engineered for vector purposes into the genome of herpes simplex type 1; J. Gen. Virol. 71:2931–2939, 1990.

J. Mclaughlan et al. "Characterisation of enveloped tegumant . . . " J. Gen. Virol., vol. 73, 1992, pp. 269–276.

F. Rixon et al. "Assembly of enveloped tegument structures . . . " J. Gen. Virol., vol. 73, 1992, pp. 277–284.

L. Nguyen et al. "Replication–defective mutants of herpes simplex virus . . . " J. Virol., vol. 66, No. 12, 1992, pp. 7076–7072.

Herpesvirus. Genetic variability and recombination. (1998). By Kenichi Umene, Published by Touka Shobo, Fukuoka. [Table 3.1; pp. 47–53].

Dolan, A, Jamieson, F.E. Cunningham, C, Barnett, B.C. and McGeoch, D.J. (1998). "The genome sequence of herpes simplex virus type 2", J. Virol 72 2010–2021.

Telford, E.A.R., Watson, M.S., McBride, K., and Davison, A.J., (1992) "The DNA sequence of equine herpesvirus–1", Virology 189, 304–316.

Davison, A.J. (1993) "Herpesvirus genes", Reviews in Medical Virology 3, 237–244.

Johnson, P.A., McLean, C., Marsden, H.S., Dalziel, R.G., and Everett, R.D. (1986). The product of gene US11 of herpes simplex virus type 1 is expressed as a true late gene. Journal of General Virology 67, 871–883.

Kibler, P.K., Duncan, J., Keith, B.D., Hupel, T., and Smiley, J.R. (1991). Regulation of herpes simplex virus true late gene expression: sequences downstream from the US11 TATA box inhibit expression from an unreplicated template. Journal of Virology 65, 6749–6760.

McGeoch D.J. Dalrymple, M.A. Davison, A.J. Dolan, A. Frame, M.C., McNab, D, Perry, L.J. Scott, J and Taylor P. (1988) The complete DNA sequence of the long unique region in the genome of herpes simplex virus type 1. Journal of General Virology 69, 1531–1574.

Davison, A.J., and Scott, J.E. (1986). The complete DNA sequence of Varicella T Zoster virus. Journal of General Virology, 67, 1759–1816, pp. 1759–1761 and 1802–1815 only.

Roizman and Sears (1990) Chapter 65 in Fields Virology vol. 2, second edition, edited by B.N. Fields and D.M. Knipe, published by Raven Press, pp. 1805–1807.

HERPESVIRUS PRE-(VIRAL DNA REPLICATION) ENVELOPED PARTICLES

This application is a national stage application of International Application No. PCT/GB95/00156, filed Jan. 25, 1995.

BACKGROUND OF THE INVENTION

1. Field of the Invention

This invention relates to a form of herpesvirus particles suitable for use in vaccination, the preparation of such particles, and vaccines containing them.

2. Description of the Related Art

Herpes simplex virus type 1 (HSV-1) light particles (L-particles) are non-infectious virus-related particles, produced in approximately equal numbers with virions throughout the virus replication cycle in BHK cells (Szilagyi and Cunningham, 1991, J. Gen. Virol. 72, 661–668; Rixon et al., 1992, J. Gen. Virol. 73, 277–284). Similar L-particles have been isolated from pseudorabies virus (PRV); equine herpesvirus type 1 (EHV-1) (McLauchlan and Rixon, 1992, J. Gen. Virol. 73, 269–276); bovine herpes virus type 1 (BHV-1); varicella-zoster virus (VZV) (Dargan and Subak-Sharpe, unpublished) and HSV-2 (MacLean, unpublished). Because of the non-infectious nature of L-particles they have great potential as candidate vaccine materials (PCT Patent Application Publication No. 92/19748).

Comparative analysis of the protein composition of HSV-1, PRV and EHV-1 L-particles and virions show that most or all the virion tegument and envelope proteins are present in L-particles, but the nucleocapsid proteins are not present. Five phosphoproteins not detectable in HSV-1 virions are associated with HSV-1 L-particles (Szilagyi and Cunningham, 1991, J. Gen. Virol. 72, 661–668; McLauchlan and Rixon, 1992, J. Gen. Virol. 73, 269–276).

HSV-1 L-particles have been shown to be as efficient as virions in supplying functional tegument proteins to target cells. Thus, L-particles are biologically competent and have the potential to participate in the early stages of HSV-1 infections (McLauchlan et al., 1992, Virology, 190, 689–688).

Using an HSV-1 ts mutant (ts1201) (Preston et al., 1983, J. Virol. 45, 1056–1064) having a mutation in gene UL26, Rixon et al., 1992, J. Gen. Virol. 73, 277–284, demonstrated that L-particles were generated independently of virion maturation. Under non-permissive conditions ts1201 failed to make infectious virions but produced L-particles which were identical to typical wild-type virus L-particles in appearance and protein composition. Although viral DNA is synthesised normally in cells infected with ts1201 under their non-permissive conditions, viral DNA packaging into virions is blocked (Preston et al., 1983, J. Virol. 45, 1056–1064).

Although L-particles can be prepared to be substantially free of infectious virions, a typical preparation of HSV-1 L-particles containing a ratio of from $3\times10^3:1$ to $1\times10^4:1$ L-particles: infectious virions, there is a problem to improve on this ratio. Further, although the L-particles lack a capsid and the DNA within it, L-particle preparations still contain some viral DNA present in contaminating virions and/or possibly in the form of free nascent viral DNA. It would be advantageous to reduce the amount of such DNA present in the L-particle preparations, in order more easily to convince regulatory authorities of the safety of a vaccine containing them.

Additional prior art, the relevance of which becomes clear only in the context of the present invention, is referred to below after "Summary of the invention".

SUMMARY OF THE INVENTION

The inventors have now found a new type of herpesvirus particles, which are herein called pre-(viral DNA replication) enveloped particles (PREPS). Like L-particles, they are non-infectious. They can be prepared reliably to have a high ratio, typically for HSV-1 from $6\times10^5:1$ to $3.8\times10^8:1$ and frequently for HSV-1 of at least $10^7:1$ PREPS:infectious virions. The underlying experimental finding is that HSV-1 PREPS can be produced under conditions where viral DNA replication is blocked either by use of drugs (e.g. Acyclovir [ACV]; Elion et al, 1977, Proceedings of the National Academy of Sciences, USA, 74, 5716); cytosine-$\beta$-D-arabinofuranoside [ara C]; (Ward and Stevens, 1975, J. Virol. 15, 71–80) or by using an HSV-1 mutant defective in viral DNA synthesis.

The data reported below show that in the absence of viral DNA synthesis HSV-1 and other $\alpha$-herpesviruses such as HSV-2 and pseudorabies virus can synthesise PREPS, but not infectious virions, from infected cells. Moreover, PREPS preparations are not expected to contain nascent (=newly synthesised) viral DNA and therefore have the advantage of generating a safer vaccine by virtue of reducing the overall amounts of viral DNA per unit of vaccine. The results indicate that PREPS may be produced by using HSV-1 mutants defective in any of its replication proteins, or in HSV-1 infected cell cultures treated with any inhibitor of viral DNA synthesis or of protein(s) essential to viral DNA replication. Although the invention is illustrated mainly by reference to HSV-1, it is a pioneer invention of general principle which can be expected to be applicable to any virus of the herpesvirus family, especially of the $\alpha$-herpesvirus family, e.g. to those referred to above in connection with L-particles. Further, the PREPS can be made to incorporate foreign proteins by recombinant DNA techniques.

Important features of the invention are (1) a virus preparation substantially free of virions, based on particles of a herpesvirus which are virus-related, non-infectious particles of a herpesvirus lacking a capsid and viral DNA, characterised in that they are pre-(viral DNA replication) particles (PREPS) lacking or containing only small amounts (smaller by comparison with corresponding L-particles) of at least one of those proteins, called "true late" proteins, which are normally produced only after replication of viral DNA, but containing larger amounts of at least one of the other viral proteins (larger by comparison with corresponding L-particles) and optionally further characterised by having fewer envelope glycoprotein spikes than L-particles, when viewed by electron microscopy; and (2) a method of preparing a virus preparation characterised by comprising infecting host cells with a herpesvirus under conditions effective to prevent replication of viral DNA, allowing the synthesis of viral proteins and PREP formation and recovering from the cells or extracellular medium a substantially virion-free preparation of virus-related, non-infectious, particles.

ADDITIONAL PRIOR ART

Very recently, Morrison and Knipe, 1994 J. Virol. 68, 689–696, have demonstrated immunisation in a mouse model against HSV-1 by direct injection with replication-defective strains of HSV-1. The mutant virus stocks contained less than 1 pfu of wild type virus per $10^7$ pfu of mutant virus as determined by assays. The viral DNA content of the mutant virus preparation was equivalent to that of wild type virus. However, these authors have not appreciated that the mutant virus stocks could be used to produce PREPS or that such PREPS could serve as vectors in which foreign proteins could be carried to generate an immune response to those proteins. In other words, these virus stocks have been produced using complementing cell lines and are at the equivalent stage to the starting inoculum used in relation to the method of the invention.

BRIEF DESCRIPTION OF THE ACCOMPANYING DRAWINGS

FIGS. 1(a) to 1(d) show "Ficoll" density gradients containing (1a) wild type control, (1b) amb UL8, (1c) Acyclovir-treated, and (1d) ara C-treated preparations, all of HSV-1. Bands corresponding to virion (V), L-particles (L) and PREPS are indicated.

FIGS. 2(a) and 2(b) show electron micrographs of HSV-1 L-and PREP particles, respectively.

FIG. 3 is a photograph of a silver-stained gel showing SDS-PAGE analysis or protein profiles of virion (V), L-particles (L) and (PREPS) (P) of HSV-1.

DESCRIPTION OF THE PREFERRED EMBODIMENTS

Figure 1A:
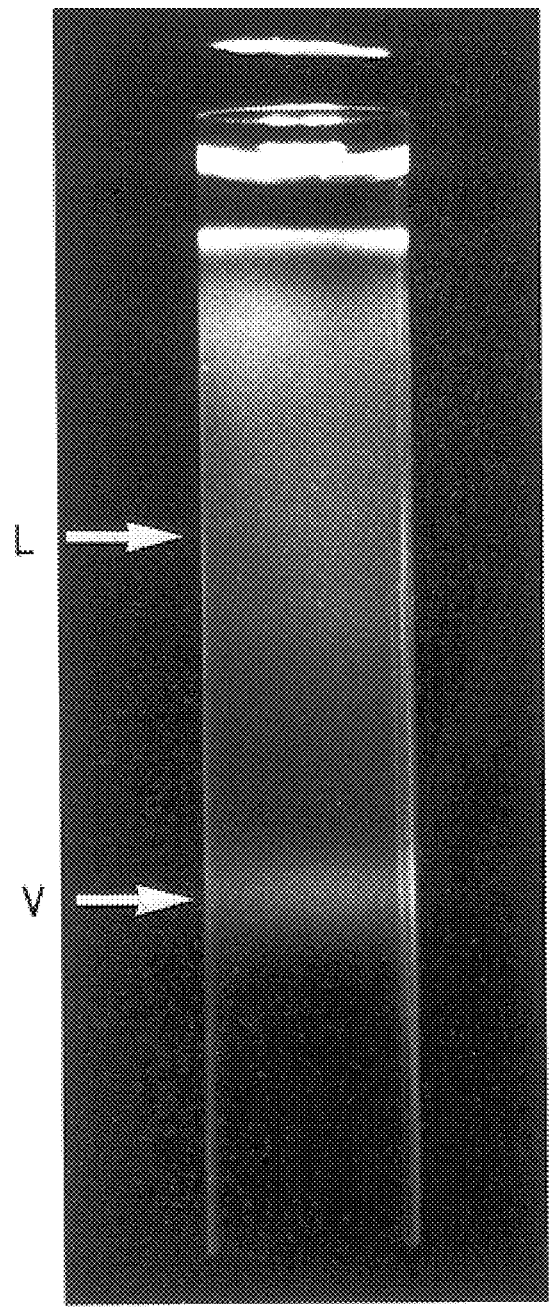
Figure 1B:
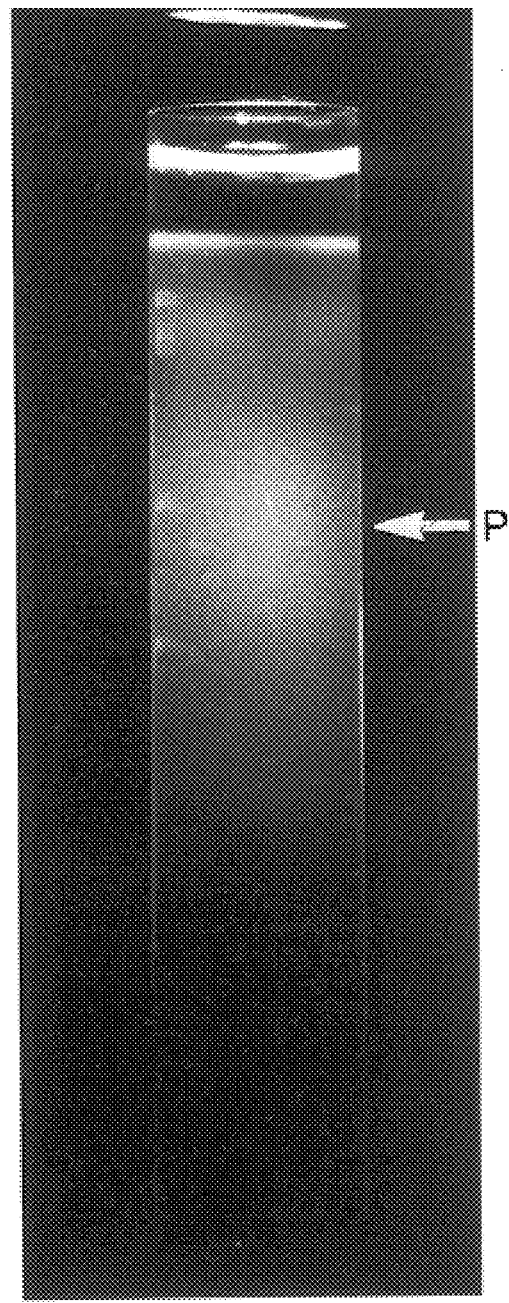

In the virus particle preparations of the invention, the numerical ratio of PREPS to infectious virions (defined as plaque-forming units) will usually be at least $7 \times 10^6:1$ and more usually at least $1 \times 10^7:1$. The number of PREPS can be determined by electron microscopy. The number of pfu can be determined by plaque assay of virus grown on monolayers of appropriate cells. The greater ratio found in PREPS compared with L-particles probably arises at least in part because no new infectious progeny are made by the PREPS, owing to the DNA synthesis inhibition. (The L-particle/virion ratio of about $10^6:1$ in small scale experiments mentioned in WO 92/19748 is not comparable with the L-particle/pfu ratio).

Considered in terms of the particles per se, these PREPS differ from L-particles in that they lack or contain in reduced amounts "true late" protein(s) (Johnson et al., 1986 J. Gen. Virol. 67, 871–883). True late proteins are made at a late stage in the virus growth cycle and are considered to result from transcription of nascent copies of the original viral DNA. Consequently, when DNA synthesis is inhibited, true late proteins are not made or only made in small amounts, i.e. smaller amounts than present in the corresponding L-particles. The "corresponding" L-particles are those obtainable from wild type virus of the same strain (i.e. disregarding any minor genetic differences).

Important true late proteins in HSV-1 are "82/81K" (VP13/14) (McLean et al., 1990, J. Gen. Virol. 71, 2953–2960), 273K (VP1–2) (McNabb and Courtney, 1992, Virology 190, 221–232) and g C (VP 8) (Peake et al., 1982, J. Virology 42, 678–690). Absence or reduction of the amount of any one or more of these proteins may be called in aid as a distinctive feature of the PREPS of HSV-1. In general, for herpesviruses, it is expected that at least one, and normally at least two true late proteins will be lacking or present in reduced amount in PREPS compared with L-particles.

For many purposes, the absence or reduced amount of true late proteins is sufficient to distinguish PREPS from L-particles. However, this distinction reflects merely the absence of replication of viral DNA by PREPS. PREPS could be made to contain true late proteins in greater amount if the viral genome were altered to put the gene(s) coding for one or more of the true late proteins under control of an "early" promoter, i.e. one which causes mRNA transcription early in the process of particle-formation, so that the true late proteins can be produced in the viral tegument of the particles. The use of an "early" viral promoter to transcribe true late proteins has been described in the literature and is therefore feasible. Since PREPS could be made to include true late proteins, the absence or reduction thereof is not distinctive of all possible PREPS. However, it has further been found that certain other viral proteins are present in increased amounts in PREPS compared with L-particles. In HSV-1, these are the 175K (VP 4, IE 3), 92/91K (VP 11/12) and 38K (VP 22) proteins. In general, for herpesviruses, it is expected that at least one, and normally at least two viral proteins will be produced in increased amounts in PREPS by comparison with L-particles.

In the method of preparation of the invention, the initiating herpesvirus inoculum has to contain DNA, because DNA is required for production of viral proteins involved in producing the particle structure (tegument proteins, envelope proteins etc.). Thus, when a viral DNA replication-negative mutant is used to synthesise PREPS, the viral inoculum itself used to initiate the treatment of cells with the virus has to be produced using some kind of helper specifically complementing for the mutant function, in order to restore full functionality for viral DNA synthesis. For example, engineered cells that express that missing function or a helper virus that expresses the function may be used.

The starting herpesvirus may be disabled in several ways to prevent DNA synthesis. This is readily achieved by introducing a deletion, insertion, variation or stop signal into DNA encoding a protein which is necessary for viral DNA synthesis. For example, in HSV-1 it is particularly effective to mutate the DNA encoding the UL8 protein. UL8, UL5 and UL52 proteins together form a complex which is associated with DNA-helicase-primase activity (Crute et al., 1989, Proc. Nat. Acad. Sci. USA, 86, 2186–2189). While this particular function is supplied by UL5 and UL52 alone (Calder et al., 1992, J. Gen. Virol. 73, 531–538), the complex also acts in some other way to enable DNA replication and UL8 is essential to that function. Other DNA replication-essential proteins in HSV-1 which could be disabled are listed in Example 3. Equivalent genes of VZV or EHV-1 respectively are VZV genes 55, 52, 51, 29, 28, 16 and 6 (Davison and Scott, 1986, J. Gen. Virol. 67, 1759–1816) and EHV-1 genes 57, 54, 53, 31, 30, 18 and 7 (Telford et al., 1992, Virology, 189, 304–316). Genes encoding DNA replication-essential proteins in other herpesviruses are known to those skilled in the art or will be determined in manners analogous to those used for HSV-1, VZV and EHV-1.

Another way to disable the starting herpesvirus is to block replication of its DNA by a specific or general chemical inhibitor of DNA synthesis such as Acyclovir, phosphonoacetic acid (PAA) or cytosine-β-D-arabinofuraroside (ara C). Their respective modes of action are documented in (Elion et al., 1977, above, Mao et al., 1975, J. Virol., 15, 1281–1283 and Mach et al., 1975, J. Virol., 15, 1281–1283).

Other forms of disablement or interference with DNA synthesis can be devised (e.g. removal or inactivation of the relevant promoter of transcription of a gene) and all forms are within the scope of the invention. The essential requirement is that the host cells be infected with herpesvirus virions and particles allowed to be synthesised under conditions effective to prevent viral DNA synthesis. For example, the inhibitory agent could be an anti-sense oligonucleotide or a peptide inhibitor binding to a protein or protein complex required for DNA synthesis; or an agent that prevents the formation of or disrupts a replication-essential protein-protein or protein-nucleic acid complex.

The process of culture includes an appropriate incubation period to allow virus specified products to be synthesised. By transcribing off the input viral DNA, envelope, tegument and various other proteins are produced, resulting in particle assembly and therefore synthesis of PREPS, but true late proteins are either only produced to a very minor (trace) extent or not at all. To reduce further the amount of infectious virions contaminating the PREP preparations, virions from the starting inoculum, which have been adsorbed onto the cells but have not penetrated them, should be removed as thoroughly as possible. Alternatively or additionally, the virions can be inactivated, for example, through an acid glycine wash, as described by Rosenthal et al., 1984, J. Virol., 49, 980–983.

The immune responses to PREP preparations are expected to provide protection against the type of herpesvirus from which the PREPS are derived. It is expected that the PREPS will induce protection against a herpesvirus infection of the strain which provides the relevant proteins of the PREPS, but there will doubtless, in many cases, result a degree of protection against other strains within a serotype or even against strains of a different serotype.

While the invention thus far described relates to PREPS wholly composed of elements of herpesvirus, a wider range of protection could be provided by producing recombinant herpesviruses expressing inserted foreign DNA in such a way as to incorporate the resulting foreign proteins or epitopic peptides from unrelated viruses or other types of herpesvirus or other organisms into the PREPS. (The term "foreign" herein means not native to the strain of herpesvirus from which the PREPS are derived).

Where the foreign DNA is foreign only in the sense that it is derived from another strain or type of HSV, it is expected that a recombinant HSV containing the foreign DNA will express it without difficulty in most cases, so that the protein thus produced becomes incorporated within the PREPS (e.g. in the envelope or in the tegument). Recombinant virus expressing the foreign protein can be constructed by inserting the gene for that protein placed under the control of appropriate HSV signals in the genome of either the wild type HSV-1 virus or the DNA-replication negative HSV-1 using standard techniques (Rixon and McLauchlan, 1993, In: Molecular Virology, A Practical Approach, p. 285–307; ed. Davison A. J. and Elliott, R. M. IRL Press, Oxford). The wild type virus carrying the foreign gene can either be used with DNA-replication inhibitors (see above) or can be engineered further to render it DNA-replication negative. PREPS containing foreign proteins could also be produced by treating cells engineered to express the foreign genes, carrying appropriate herpesvirus signals, with the DNA-replication negative HSV-1 or with wild type HSV in the presence of DNA replication inhibitors.

The cells or specifically constructed HSV mutant complementing cell lines can be any appropriate to vaccine use and approved by regulatory authorities. They may be, for example, baby hamster kidney cells. Complementing cell lines are purely to grow the defective virus to be used as inoculum which in turn is used to infect non-complementing cells for PREP production. The infected culture is then incubated, preferably for at least 24 hours, to produce PREPS containing foreign protein or a peptide expressed from the recombinant herpesvirus DNA, substantially free of virions. The above description applies *mutatis mutandis* to other herpesviruses.

The particle preparations of the invention are normally produced in a cell-free form. That is, the PREPS are separated from the supernatant of cells from which they have been excreted or recovered from cells containing them. Thus, the preparations are desirably made as far as possible free of whole cells and of cell debris.

To maximise the potential use of PREPS, considerable interest centres on the expression of foreign genes not native to HSV, e.g. of other herpesviruses such as human cytomegalovirus (HCMV) or varicella zoster virus (VZV), or of unrelated viruses, e.g. immunodeficiency group viruses or papillomaviruses, or of bacterial or non-viral parasites. It may be necessary to engineer the foreign DNA to provide it with HSV signals such that the expressed protein is targeted to the PREPS. This engineered foreign DNA can then be incorporated into an appropriately chosen site or region of the herpesvirus genome. Finding the signals for targeting into the PREPS will be a matter of trial and error, but it has already been shown in Example 3 of WO 92/19748 that the virion host shut-off (vhs) protein gene of HSV-1 is capable of providing the requisite signals for targeting into L-particles. Experimentation with marker genes along the lines indicated in that Example will readily provide appropriate herpesvirus genomic sequences for the construction of required recombinants.

Examples of the foreign proteins and peptides or heterologous antigens which can be introduced into HSV-1 PREPS by procedures as described above are any HSV-2 structural proteins, or other proteins, such as gD2, gB2, immediate-early Vmw 183, or HSV-2 equivalent of Vmw 65, etc and proteins of other herpesviruses such as HCMV gB etc., or of unrelated viruses such as human immunodeficiency virus proteins (or peptides), such as of HIV-1 or HIV-2 gp 120 or gp 160, etc., or proteins in nature produced by any prokaryote or eukaryote.

If it is found that the presence of one or more HSV-1 true late proteins is helpful in PREPS to improve their immunogenic or other properties, it would be possible to re-introduce these genes under the control of appropriate early or immediate early promoters into the genome of a viral DNA-replication negative virus. Under such conditions, these true late proteins are expected to be expressed as early or immediate early gene products.

There are several references to work done in putting early genes under control of an immediate-early promoter in HSV-1 and obtaining competent viral particles, see e.g. L. E. Post et al., 1981, Cell 24, 555–565 and 25, 227–232, J. M. Calder et al., 1992, J. Gen. Virol. 73, 531–538 and H. M. Weir et al., 1989, Nucleic Acids Research 17, 1409–1425. Further it is known that true late genes can be put under control of early or immediate-early promoters in bacterial plasmids. The man skilled in the art will therefore be able to combine these technologies and apply them to the present invention.

The vaccine of the invention may be of any formulation by which PREPS can stimulate formation of antibodies to the relevant proteins and/or stimulate cell-mediated immunity. The vaccine will therefore frequently contain an immunostimulant (e.g. adjuvant) or vehicle, as well as a virus particle preparation of the invention. It can, of course, also contain other conventional additives, such as excipients and assistant adjuvants. The PREP particles in the vaccine can be in untreated form or in a form in which they have been irradiated or, treated chemically with agents like formaldehyde. Irradiated or chemically treated PREP vaccines could be used whole or possibly in a disrupted or comminuted form to release proteins from the tegument. The vaccine is desirably made up into unit dosage forms. Appropriate doses can be derived from knowledge of the use of herpesvirus vaccines, e.g. of HSV-1 or VZV virus, but the dose will also depend on whether the PREPS are intended to protect against a herpesvirus infection or mainly to stimulate the immune system with an immunogenic foreign protein or peptide. In the latter case, dosages appropriate to the foreign protein or peptide will have to be calculated, using the existing body of knowledge concerning that protein or peptide.

For administration of the preparations of the invention to the appropriate mammals, any of the conventional routes used in the viral vaccine field can be used. These will be predominantly by subcutaneous or intramuscular injection, but other routes, e.g. oral, intravenal, intravaginal, intraperitoneal and intranasal, may be more appropriate on occasions. They can be administered for the prophylactic or therapeutic vaccination against herpesvirus or, if foreign protein is incorporated in the PREPS to stimulate the immune system to increase an immunoprotective effect against it. In this context, the invention is expected to be useful in the prophylaxis of AIDS in HIV-negative, at risk individuals.

The invention is primarily intended for use in human patients, in which case the herpesvirus is preferably one likely to be tolerated by humans when in the form of non-infectious particles, especially a herpes simplex virus and most especially HSV-1.

However, for use in other animals than humans, other kinds of herpesvirus may be more appropriate, e.g. equine herpesvirus for horses.

The following Examples illustrate the invention. "Ficoll" and "Sorval" are Registered Trade Marks.

EXAMPLE 1

HSV-1 PREPS produced in infected cell cultures treated with inhibitors of DNA synthesis Confluent roller bottle cultures of BHK-21cells ($2 \times 10^8$ cells/roller bottle) were infected with HSV-1 strain 17 at a m.o.i. of 5 pfu/cell in 15 ml of Glasgow-modified Eagle's medium supplemented with 5% newborn calf serum ($EC_5$). The cells were allowed 2 h at 37° C. to absorb the virus. The inoculum was then decanted and the cell sheet washed with acidic glycine to inactivate residual input virus. The washing procedure for each roller bottle was as follows (Rosenthal et al., 1984, J. Virol. 49, 980–983):

1. Wash once with 20 ml of 0.14M NaCl.
2. Wash once with 20 ml of 0.1M glycine pH 3.0 in 0.14M NaCl for 1 min.
3. Wash once with 20 ml of $EC_5$ to neutralise the acid.

The cells were then overlaid with 30 ml/roller bottle of drug-free $EC_5$ or of $EC_5$ containing 10 $\mu$M Acyclovir (ACV) (Sigma) or 100 $\mu$g/ml cytosine-$\beta$-D-arabinofuranoside (ara C) (Sigma). The infected cultures were then grown at 31° C. for 48 h before harvesting.

The extracellular material was clarified (4000 rpm for 20 min/4° C.) using a "Sorval" GSA rotor, and pelleted (12000 rpm/2 h/4° C.) using the same rotor (Szilagyi and Cunningham, 1991, above). This provided cell-released particles.

After gentle resuspension of the pelleted material it was separated by density gradient centrifugation using the procedure of Szilagyi and Cunningham (1991, above).

Figure 1C:
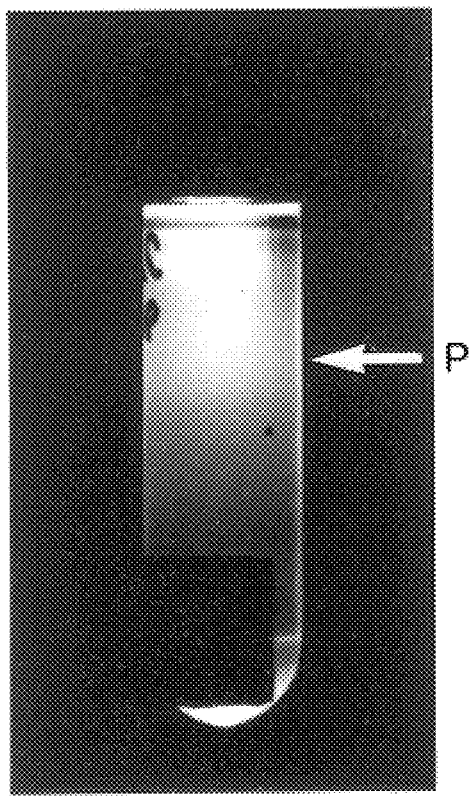
Figure 1D:
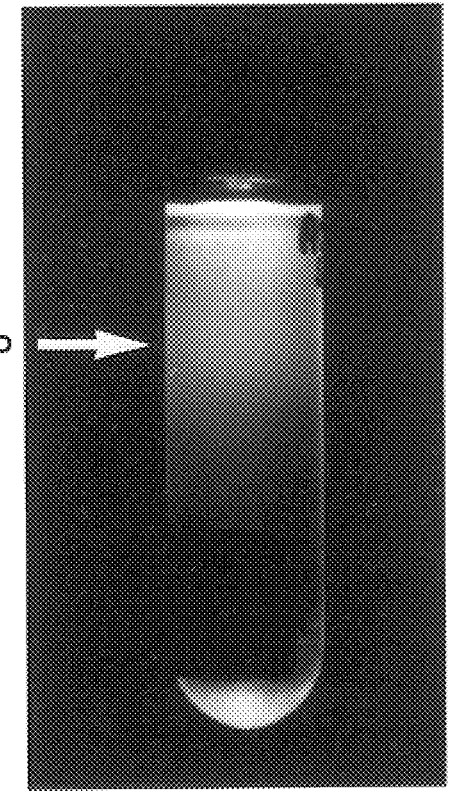

The "Ficoll" gradients containing the drug-free preparation yielded bands of characteristic virions and L-particles, while the gradients containing material produced in the presence of ACV and ara C had no visible virion band, although a diffuse band corresponding to the drug-free "L-particle" band was present (FIGS. 1c and 1d).

These bands were collected by side-puncture, made up to 37 ml with Eagle's medium lacking phenol red (Epr⁻), pelleted by centrifugation at 19,000 g for 16 h at 4° C. in a Sorval AH 629 rotor and subsequently resuspended in a small volume of Epr⁻ and stored at -70° C. The material was subsequently examined by electron microscopy, which showed high numbers of particles resembling wild type L-particles (FIGS. 2c and d). The particles made in the absence of viral DNA replication have been designated PREPS. The region of the gradients corresponding to the location of the virion band in the drug-free preparation was similarly removed and analysed. The analysis is presented after Example 4.

Similar results were obtained using infected cell extract material containing intracellular PREPS, released from cells by mechanical breakage with glass beads and purified as described above.

EXAMPLE 2

BHK cells or human melanoma cells (MeWO) were grown in Eagle's medium supplemented with 10% newborn calf serum or Dulbecco's modified Eagle's medium supplemented with 10% foetal calf serum ($DMEM_{10}$) respectively. The drugs (10 $\mu$M ACV, 100 $\mu$g/ml Ara C or 300 $\mu$g/ml PAA) were added 1 h prior to infection and were present throughout infection with HSV-1. Following incubation at 37° C., PREPS were purified from the medium, as described in Example 1.

It has been found that the temperature at which the infected cells are grown is of minor importance so long as the cells reach the full cytopathic effect (cpe) condition, which is well understood by the person skilled in the art and can be judged visually by the cells losing their stringy appearance and becoming fully round. Either 31° C. for 48 hours or 37° C. for 24 hours was used in this Example.

The resulting PREPS were analysed, as described after Example 4.

EXAMPLE 3

Isolation of a DNA replication-negative amber non-sense mutant of HSV-1

HSV-1 gene nomenclature and DNA sequence are set forth by McGeoch et al., 1988, J. Gen. Virol. 69, 1531–1574.

HSV-1 genes UL5, UL8, UL9, UL29, UL30, UL42 and UL52 encode proteins which are known to be required for viral DNA synthesis in tissue culture cells (Wu et al., 1989, J. Gen. Virol. 62, 435–443; Weller et al., 1991, In: Herpesvirus Transcription and its Regulation, 105–135). Mutations which abolish the function of any one of these genes fail to induce viral DNA synthesis in infected cells. The biochemical functions so far assigned to these replication proteins are as follows. The products of UL5, UL8 and UL52 form a heterotrimer complex which exhibits DNA helicase-primase activities (Crute et al., 1989, Proceedings of the National Academy of Sciences, USA 86, 2186–2189). Gene UL9 encodes an origin-binding protein (Weir et al., 1989, Nucleic Acids Research, 17, 1409–1425); UL29 encodes the major DNA-binding protein (Weller et al., 1983, J. Gen. Virol. 45, 354–366); UL30 and UIL42 respectively encode the viral DNA polymerase and its accessory protein (Dorsky et al., 1987, J. Gen. Virol. 61, 1704–1707; Parris et al., 1988, J.

Virol. 62, 818–825; Wu et al., 1988, above; Marcy et al., 1990, Nucleic Acids Research, 18, 1207–1215).

In order to construct a HSV-1 mutant defective in viral DNA synthesis, the serine codon at amino acid position 267 of the UL8 protein was replaced with an in-frame amber stop codon by in vitro site-directed mutagenesis. The mutated gene was then introduced into the wild type virus genome by homologous recombination. The resultant mutant virus, HSV-1 ambUL8, was isolated in a permissive cell line (S22) which was generously supplied by Dr S. Weller (Carmichael et al., 1988, J. Virol., 62, 91–99), but the cell line A26 (below) could equally be used. The amb UL8 mutant failed to produce plaques or synthesise viral DNA when grown in Vero cells, consistent with the observation made previously that UL8 is essential for viral DNA synthesis (Carmichael and Weller, 1989, J. Virol., 63, 591–599). The efficiency of ambUL8 virus production in Vero and S22 cells, as measured by single-step growth analysis, showed that the mutant failed to grow on Vero cells whereas the virus yield on S22 cells was comparable to that of wild type virus. Western immunoblot analysis using monoclonal antibodies specific for UL8 protein failed to detect the UL8 gene product in ambUL8-infected Vero cells. For the work reported herein the virus was propagated in another complementing cell line (A26 cells derived from Vero cells) which was constructed as follows.

Following the procedure of DeLuca et al., 1985, J. Virol. 56, 558–570, Vero cells were co-transfected with a plasmid carrying the Bgl11 k fragment of the HSV-1 genome (co-ordinates 14589 to 25149 containing the complete nucleotide sequences of HSV-1 genes UL6, UL7, UL8, UL9 and UL 10; McGeoch et al., 1988, above) and another plasmid, pSV2neo, containing the neomycin resistance gene under the control of the simian virus 40 (SV40) promoter (Southern and Berg. 1982, J. Mol. Appl. Genet. 1, 327–341). The transfected cells were grown to confluence, trypsinised and plated at 1:25 dilution in medium containing 800 μg/ml of the antibiotic Geneticin (G418, GIBCO BRL). Following incubation at 37° C. for 2 weeks (with periodic change of medium), individual colonies resistant to G418 were visible. These colonies were isolated and amplified. One of the colonies was chosen and found to be able to support the growth of a HSV-1 amb UL8 mutant which formed plaques and displayed cpe on this cell line, which was designated A26. The A26 cell line was also able to support the growth at 38.5° C. of a temperature-sensitive mutant, tsS in UL9, (Marsden et al., 1976, J. Gen. Virol. 31, 347–372; Dargan and Subak-Sharpe, 1983, J. Gen. Virol. 64, 1311–1326).

The ability of ambUL8 virus to synthesise virus-like particles under non-permissive conditions (i.e. under conditions non-permissive for HSV-1 DNA replication, using a non-complementing cell line) was examined. BHK cells in roller bottles were infected with ambUL8 or wild type virus at an m.o.i. of 5 pfu./cell, followed by acid glycine wash as described in Example 1 above. Infected cells were incubated further at 37° C. for 3.5 h in Eagle's medium containing 2% calf serum ($EC_2$). Cell medium was then replaced with methionine-free $EC_2$, containing 0.5 mci $^{35}$S-methionine (for purposes of autoradiography, superseded by silver staining: see Example 4) and incubation was continued for a further 43 h. Extracellular matter present in the supernatant medium was pelleted, resuspended and analysed in a 5–15% "Ficoll" gradient as described by Szilagyi and Cunningham (1991, above). The wild type virus preparation gradient contained bands corresponding to virions and L-particles. In the ambUL8 preparation gradient, the virion band was absent, although a diffuse upper band corresponding to the L-particle band of wild type virus was present (FIGS. 1a and b). In the gradient containing ambUL8, material co-migrating with the wild type virion band was also collected. The analysis is described below.

EXAMPLE 4

PREPS from ambUL8 HSV-1 were prepared from virus-treated BHK and MeWO cells, following the conditions of Example 2 for all stages, except that no drugs were used.
Analysis of PREPS
Negative-stain electron microscopy 5 μl samples of L-particles or PREPS were spotted on to a "Formvar"-coated EM grid and allowed to dry. The grid was then treated with 5 μl of phosphotungstic acid (PTA) for 5 seconds and excess PTA was removed by blotting. The samples were examined in a "Jeol" 101 electron microscope.

Figure 2A:
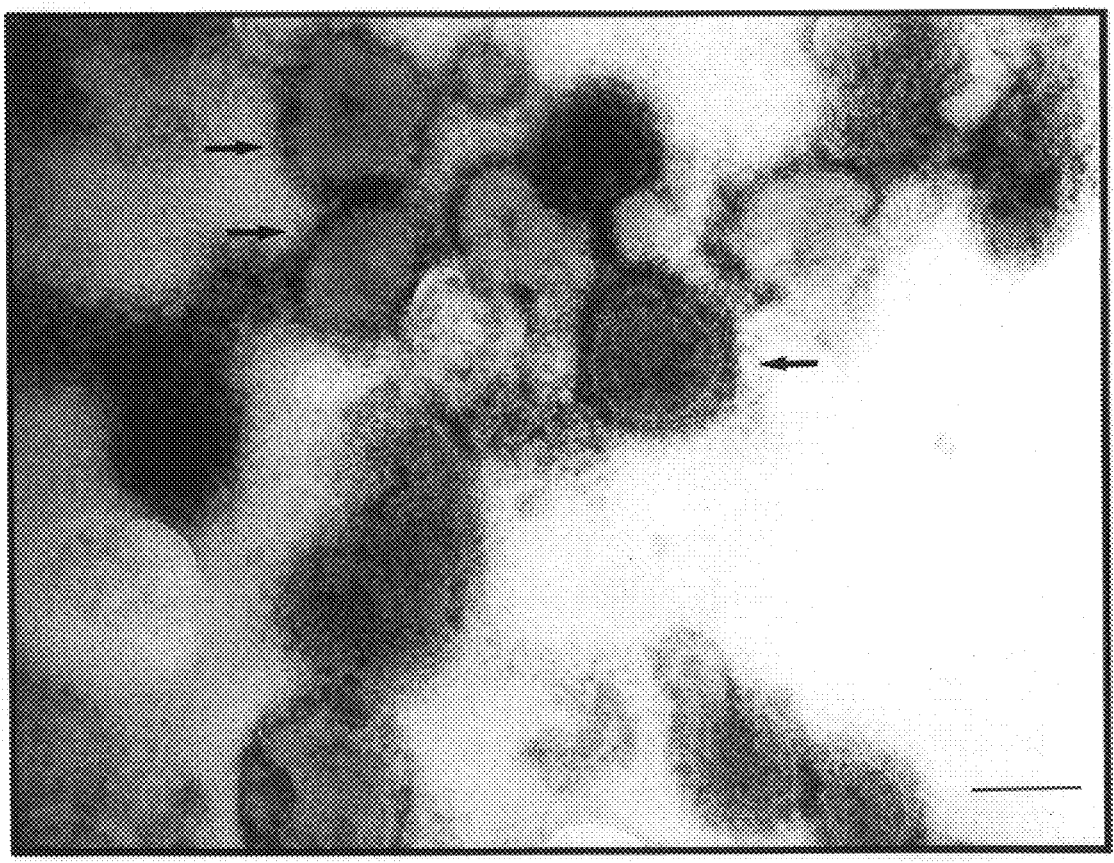
Figure 2B:
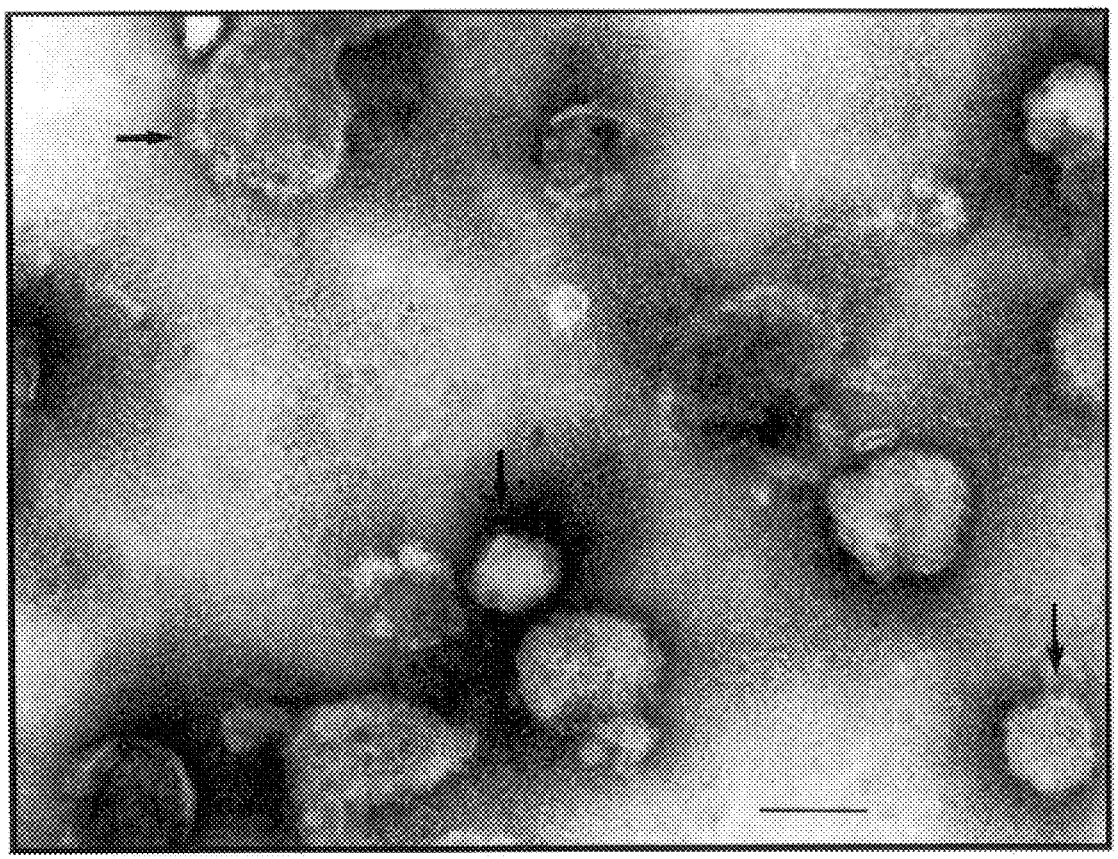

By electron microscopy, careful study of HSV-1 L-particles has revealed a difference in appearance between L-particles and PREPS: in PREPS the envelope glycoprotein spikes were less numerous per particle. The difference can be seen by careful scrutiny of the EM photographs of FIGS. 2a and 2b, showing the stained L-particles and PREPS respectively (from Example 4, but those from the other Examples are similarly distinguishable). Typical particles in which these spikes are clearly visible are arrowed. Gaps appear between the spikes in FIG. 2b. The bar line shown is a distance of 100 nanometres.

Glycoprotein spikes are carried by all herpesviruses. It is believed and expected that the same trait will be visible in EM photographs of L-particles and PREPS of other such viruses besides HSV-1.
Infectivity Samples of the collected PREPS were titrated on BHK or A26 cell monolayers to determine the infectivity in pfu/ml. Numbers of particles/ml were determined by electron microscopy.

The results are shown in the Table. Those for the BHK cells in Examples 1 and 2 are the same and those for Examples 3 and 4 are also the same. They are presented in the Table.

Although present in insufficient number to constitute a visible band in PREPS-containing gradients, some virion particles were detected by electron microscopy by sampling in the region corresponding to the WT control virion band. The PREPS were produced in similar numbers to WT control L-particles by both BHK and MeWO cultures, irrespective of whether viral DNA synthesis was blocked biochemically by drugs or genetically. A small amount of infectivity was found in all PREPS preparations but the particle:pfu ratios obtained were routinely 100- to 10,000-fold greater than that of the WT control L-particle preparations. The high particle:pfu ratios obtained for the PREPS band and the EM-detected virions from PREPS gradients indicate that most of the virions present were non-infectious, probably representing adsorbed, acid-inactivated, inoculum virus persisting in the cultures, despite the washing procedures, and later released from the cell surface. Small amounts of infectivity were found in association with the PREPS, but fewer than for L-particles.

TABLE

HSV-1 VIRION, L-PARTICLES AND PREP PARTICLE AND INFECTIVITY MEASURES

| Cells | Virus | Drug | L-Particle/PREPS Band | | | Virion Region | | |
|---|---|---|---|---|---|---|---|---|
| | | | P/ml | pfu/ml | P/pfu | P/ml | pfu/ml | P/pfu |
| BHK | WT | None | $9.0 \times 10^{11}$ | $8.2 \times 10^{7}$ | $1.0 \times 10^{4}$ | $6.5 \times 10^{11}$ | $4.9 \times 10^{9}$ | 138 |
| BHK | WT | ACV | $3.6 \times 10^{11}$ | $1.0 \times 10^{4}$ | $3.6 \times 10^{7}$ | $1.1 \times 10^{9}$ | $2.0 \times 10^{4}$ | $5.3 \times 10^{4}$ |
| BHK | WT | Ara C | $3.5 \times 10^{11}$ | $1.6 \times 10^{4}$ | $2.2 \times 10^{7}$ | $6.6 \times 10^{9}$ | $1.5 \times 10^{5}$ | $4.4 \times 10^{4}$ |
| BHK | ambUL8 | None | $1.8 \times 10^{11}$ | $1.0 \times 10^{4}$ | $1.8 \times 10^{7}$ | $<10^{8}$ | $3.5 \times 10^{4}$ | $>3 \times 10^{3}$ |
| MeWO | WT | None | $2.3 \times 10^{11}$ | $7.4 \times 10^{7}$ | $3.1 \times 10^{3}$ | $1.3 \times 10^{11}$ | $3.4 \times 10^{9}$ | 38 |
| MeWO | WT | ACV | $3.0 \times 10^{11}$ | $5.0 \times 10^{5}$ | $6.0 \times 10^{5}$ | $4.3 \times 10^{9}$ | $4.0 \times 10^{4}$ | $1.1 \times 10^{5}$ |
| MeWO | WT | Ara C | $10.0 \times 10^{11}$ | $2.7 \times 10^{3}$ | $3.8 \times 10^{8}$ | $8.7 \times 10^{8}$ | $2.0 \times 10^{3}$ | $4.3 \times 10^{5}$ |
| MeWO | WT | PAA | $3.9 \times 10^{11}$ | $1.8 \times 10^{4}$ | $2.1 \times 10^{7}$ | $8.8 \times 10^{10}$ | $5.4 \times 10^{5}$ | $1.6 \times 10^{5}$ |
| MeWO | ambUL8 | None | $9.6 \times 10^{11}$ | $1.3 \times 10^{5}$ | $7.4 \times 10^{6}$ | $5.4 \times 10^{9}$ | $4.4 \times 10^{6}$ | $1.2 \times 10^{3}$ |

Polyacrylamide gel electrophoresis, silver staining of proteins and western immunoblotting Purified virions, L-particles or PREP particles were solubilised and $2 \times 10^9$ equivalents loaded onto 9% SDS PAGE gels (Marsden et al., 1976, J. Gen. Virol. 31, 347–372). Proteins were visualised by silver staining as described by McLean et al., 1990, J. Gen. Virol. 71, 2953–2960.

Figure 3:
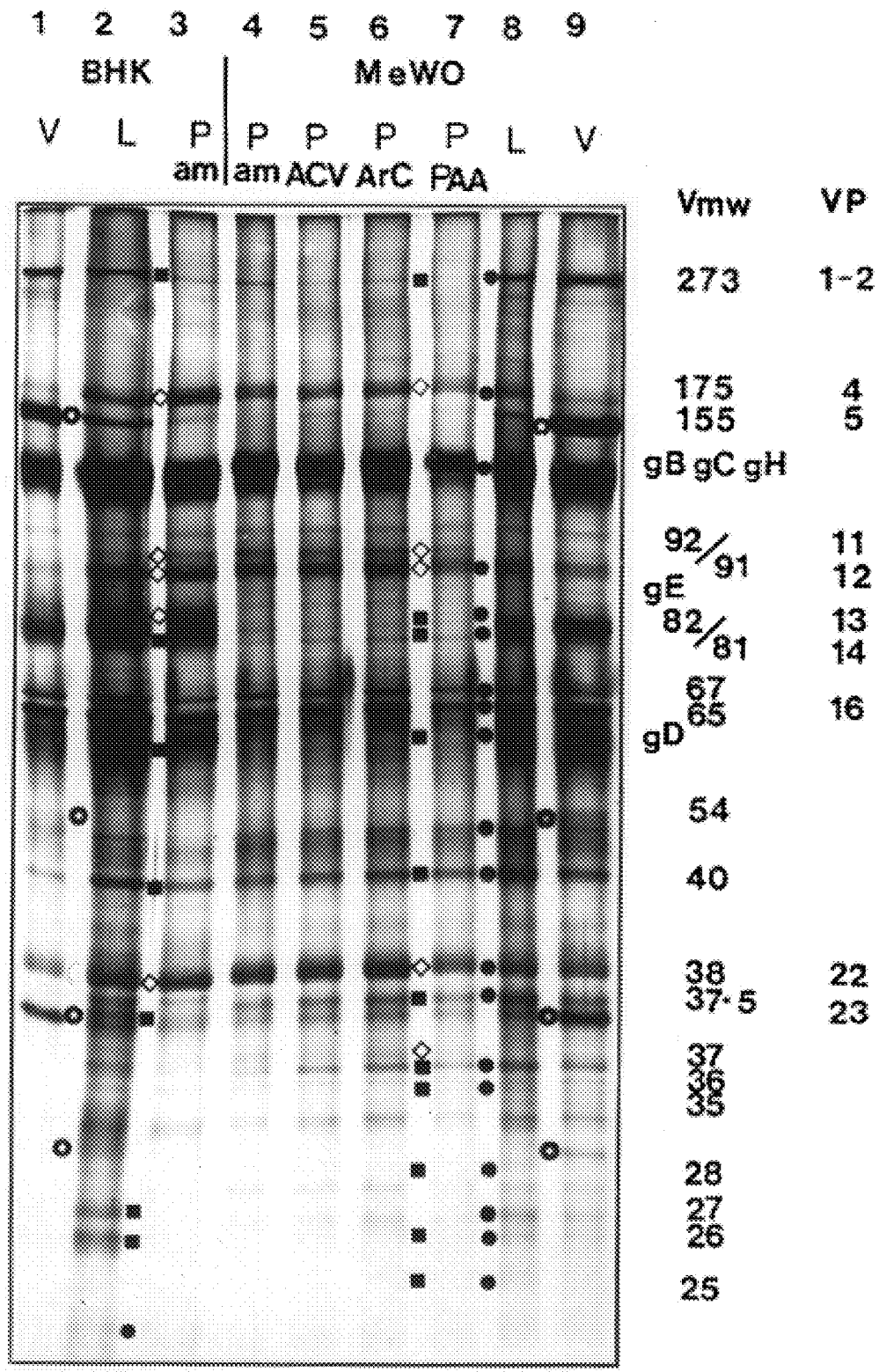

FIG. 3 shoes the polypeptide profiles as follows:
Track 1 (V) Virions from untreated WF-infected BHK cells (Ex. 2)
Track 2 (L) L-particles from BHK cells (Ex. 2)
Track 3 (P am) PREPS from ambUL8-infected BHK cells (Ex. 4)
Track 4 (P am) PREPS from ambUL8-infected MeWO cells (Ex. 4)
Track 5 (P ACV) PREPS from Acyclovir-treated WF-infected MeWO cells (Ex. 2)
Track 6 (P arc) PREPS from ara c-treated WT MeWO cells (Ex. 2)
Track 7 (P PAA) PREPS from PAA-treated WT-infected MeWO cells (Ex. 2)
Track 8 (L) L-particles from untreated WT-infected MeWO cells (Ex. 2)
Track 9 (V) Virions from untreated WT-infected MeWO cells (Ex. 2)
Key to symbols in FIG. 3:
Filled circles denote L-particle protein bands.
Open circles denote capsid protein bands.
Filled squares denote PREPS protein bands of greater intensity than corresponding L-particle protein bands.
Open diamonds denote PREPS protein bands of less intensity than corresponding L-particle protein bands.

In many respects, the profiles of PREPS and WT L-particles were similar (compare tracks 2 and 3 and also 8 and 4). However, the following significant differences in bands were consistently observed irrespective of whether the preparations were obtained from infected BHK or MeWO cells. Protein bands of 273K (VP1–2), 82/81K (VP13/14), 57K (VP17, gD), and 40K were clearly reduced in amount, although BHK-produced PREPS contained much more 81/82 and gD than those made in MeWO cells. Bands of 175K (VP4, IE3), 92/91K (VP11/12), and 38K (VP22) were increased in amount.

Solubilisation of envelope proteins

Approximately $4 \times 10^{10}$ virions, L-particles and PREPS (as for FIG. 3) were treated with 1% NP40 in EPr⁻ at 0° C. for 30 minutes. Soluble (envelope) supernatant and insoluble pellet (tegument) fractions were then separated by centrifugation at 13,000 rpm for five minutes in an MSE microfuge. After solubilisation in sample buffer (Marsden et al, 1976, Journal of General Virology 31, 347–372) a volume equivalent to $4 \times 10^9$ particles was loaded into individual gel tracks.

The following proteins were increased in amounts in the tegument fractions of PREPS; 175K multiple band (VP4; IE3), 120K, 118K, 92/91K (VP11/12), gE (BHK cells only), 67K (VP15) (MeWO), and 38K (VP22), while the 273K (VP1–2) and 82/81K (VP13/14), 40K (MeWO) and 37.5K (MeWO) were decreased. In the envelope fraction the band representing gB and gH, shows little or no difference in the amounts of these proteins in L-particles and PREPS. The amount of gD present in PREPS was, however, reduced. Glycoprotein gE appeared to be either missing or only in trace amounts in all types of particle made in MeWO cells while the amount of gE detected in ambUL8 PREPS produced in BHK cells was clearly increased compared to L-particle control.

For Western immunoblotting, envelope and tegument proteins separated by SDS PAGE were transferred to "Hybond-ECL" nitrocellulose sheets (Amersham), treated with blocking buffer (phosphate-buffered saline containing 0.05% Tween 20 (PBS-T) and 2% "Marvel" milk powder) overnight and, after washing with PBS-T, incubated with test mouse monoclonal, or rabbit-polyclonal antibodies prepared in PBS-T containing 1% bovine serum albumin for two hours at 18° C. After further washes with PBS-T, the blots were treated with anti-mouse or anti-rabbit IgG-horseradish peroxidase (as appropriate), and the tagged proteins detected by enhanced chemiluminescence (Amersham). The antibodies used were monoclonal antibody (MAB) 4846 (anti-gD); MAB 3114/109 (anti-gE); and rabbit polyclonal antibodies 94497 (anti-82/1K).

The main results of the Western immunoblotting were as follows:

The true late protein 82/81K was present in the tegument of virions and L-particles made in the BHK or MeWO cell line but, was absent from all PREPS (however prepared). Another true late protein, gC, was present in substantial amounts in the envelope fractions of both L-particles and virions, but in much lower amounts in PREPS, suggesting either that a small amount of viral DNA synthesis took place, or that some gC was produced from the input genomes. Anti-gD was slightly reduced in amount in PREPS.

Complementation of a HSV-1 cell line defective in Vmw 65K protein production

In this experiment, the ability of PREPS to complement the HSV-1 Vmw65K (α-TIF, VP16) defective mutant in1814 (Ace el al., 1988, J. Gen. Virol. 69, 2595–2605 and 1989, J. Virology 63, 2260–2269). It has been shown already that the Vmw65K tegument protein appears to be present in similar quantities in L-particles and PREPS (FIG. 3, lanes 1–9). McLauchlan et al, 1992, J. Gen. Virol. 73, 269–276 have shown that L-particles are as effective as virions at complementing the in1814 mutant.

Human foetal lung cell monolayers (Flow 202) (propagated in GMEM supplemented with 10% FCS) on 24 well tissue culture dishes were infected with in1814 at 0.1, 1.0 or 10 pfu/well. After a 1 hour absorption period, virus not taken up was removed by washing the cells with containing PBS containing 5% FCS and the monolayers then treated for 1 hour at 37° C. with 0.1, 1.0 10 or 100 particles/cell of either HSV-1 L-particles or PREPS. After three washes with PBS containing 5% FCS to remove unbound particles, the monolayers were overlaid with $EC_5$, incubated at 37° C. for 48 hours, then fixed, stained and the numbers of plaques counted.

Neither L-particles nor PREPS by themselves had any detectable infectivity, but each was able to complement the in1814 mutant. However the efficiency of PREPS complementation was about 10–30% that of control L-particles.

EXAMPLES 5 AND 6

These two examples relate to preparation of PREPS of HSV-2 from MeWO cells and pseudorabies virus from BHK cells in the presence of 100 μg/ml of ara-C and L-particles in the absence thereof. The procedure was as in Example 2, the incubation of the infected cells being at 37° C. for 48 hours. The viral strains used were HSV-2 strain HG52 (Tinbury, 1971, J. Gen. Virol. 13, 373–376) used in the MRC Virology Unit at the University of Glasgow, Scotland and a wild type pseudorabies stock also used in the MRC Virology Unit. These and all other starting viral strains and the A26 cell line herein referred to are available from The Director, MRC Virology Unit, Institute of Virology, Church Street, Glasgow G11 5JR, Scotland.

The resultant PREPS and L-particles appeared by electron microcopy to be similar to HSV-1 PREPS, having fewer glycoprotein spikes around the envelope. Polypeptide composition analysis has not yet been done, but it is confidently expected that the PREPS will again be characterised by reduced amounts of true late proteins relative to the corresponding L-particles.

We claim:
1. A composition comprising non-infectious herpes simplex virus-1 (HSV-1) pre-viral DNA replication enveloped particles (PREPS) wherein said particles have the following characteristics: (a) the PREPS lack a viral capsid; (b) the PREPS lack viral DNA; (c) the PREPS contain reduced quantities of the proteins 273K (VP1–2), 82/81/K (VP13/14), 57K (VP17, gD), and 40K, as compared to HSV-1 L-particles; and (d) the PREPS contain increased quantities of the proteins 175K (VP4, IE3), 92/91K (VP11/12), and 38K (VP22), as compared to HSV-1 L-particles.

2. The composition of claim 1, which further comprises infectious HSV-1 virions, wherein the ratio of non-infectious particles to infectious virions is at least $10^7:1$.

3. A method of preparing non-infectious herpes simplex virus-1 (HSV-1) pre-viral DNA replication enveloped particles (PREPS) wherein said particles have the following characteristics: (a) the PREPS lack a viral capsid; (b) the PREPS lack viral DNA: (c) the PREPS contain reduced quantities of the proteins 273K (VP1–2), 82/81/K (VP13/14), 57K (VP17, gD), and 40K, as compared to HSV-1 L-particles; and (d) the PREPS contain increased quantities of the proteins 175K (VP4, IE3), 92/91K (VP11/12), and 38K (VP22), as compared to HSV-1 L-particles, said method comprising infecting host cells with HSV-1 to form a culture, adding to the culture a chemical inhibitor of DNA synthesis in an amount effective to prevent HSV-1 viral replication, and recovering said PREPS from said culture.

4. A method of preparing non-infectious herpes simplex virus-1 (HSV-1) pre-viral DNA replication enveloped particles (PREPS) wherein said particles have the following characteristics: (a) the PREPS lack a viral capsid; (b) the PREPS lack viral DNA; (c) the PREPS contain reduced quantities of the proteins 273K (VP1–2), 82/81/K (VP13/14), 57K (VP17, gD), and 40K, as compared to HSV-1 L-particles; and (d) the PREPS contain increased quantities of the proteins 175K (VP4, IE3), 92/91K (VP11/12), and 38K (VP22), as compared to HSV-1 L-particles, said method comprising infecting a culture of host cells with an HSV-1 UL8 mutant that is defective in a manner effective to prevent viral DNA synthesis, and recovering said PREPS from said culture.

* * * * *